United States Patent
Yi et al.

(10) Patent No.: US 11,915,822 B2
(45) Date of Patent: Feb. 27, 2024

(54) MEDICAL IMAGE READING ASSISTANT APPARATUS AND METHOD FOR ADJUSTING THRESHOLD OF DIAGNOSTIC ASSISTANT INFORMATION BASED ON FOLLOW-UP EXAMINATION

(71) Applicant: Coreline Soft Co., Ltd., Seoul (KR)

(72) Inventors: Jaeyoun Yi, Seoul (KR); Donghoon Yu, Gimpo-si (KR); Yongjin Chang, Incheon (KR); Hyun Gi Seo, Goyang-si (KR)

(73) Assignee: Coreline Soft Co., Ltd., Seoul (KR)

( * ) Notice: Subject to any disclaimer, the term of this patent is extended or adjusted under 35 U.S.C. 154(b) by 275 days.

(21) Appl. No.: 17/538,627

(22) Filed: Nov. 30, 2021

(65) Prior Publication Data
US 2022/0172826 A1 Jun. 2, 2022

(30) Foreign Application Priority Data
Nov. 30, 2020 (KR) .................. 10-2020-0164594

(51) Int. Cl.
G16H 30/40 (2018.01)
G16H 30/20 (2018.01)
G16H 50/20 (2018.01)

(52) U.S. Cl.
CPC ............. *G16H 30/40* (2018.01); *G16H 30/20* (2018.01); *G16H 50/20* (2018.01)

(58) Field of Classification Search
CPC ......... G16H 30/40; G16H 30/20; G16H 50/20
See application file for complete search history.

(56) References Cited

U.S. PATENT DOCUMENTS 6,937,776 B2 * 8/2005 Li ........................... G06T 5/002
 382/131
7,136,518 B2 * 11/2006 Griffin .................. G01N 21/31
 382/128

(Continued)

FOREIGN PATENT DOCUMENTS

KR 10-2007-0098647 A 10/2007
KR 10-1241060 B1 3/2013

(Continued)

OTHER PUBLICATIONS

Liu, 2014, Elsevier, pp. 555-566.*
Wismueller, Handbook-of-Medical-Image-Processing-and-Analysis, 2009, Chapter 7.*

*Primary Examiner* — Michael I Ezewoko
(74) *Attorney, Agent, or Firm* — United One Law Group LLC; Kongsik Kim; Jhongwoo Peck (57) ABSTRACT

Disclosed herein is a medical image reading assistant apparatus. The medical image reading assistant apparatus includes a computing system. The computing system includes: a receiver interface configured to receive a first medical image and a second medical image following the first medical image; and at least one processor configured to: generate follow-up information between first findings on the first medical image and second findings on the second medical image by comparing the locations of the first findings and the locations of the second findings; select at least some of the first findings as first valid findings based on a first threshold of diagnostic assistant information for each of the first findings; set a second threshold of diagnostic assistant information for each of the second findings based on the follow-up information; and select at least some of the second findings as second valid findings based on the second threshold.

14 Claims, 6 Drawing Sheets (56) References Cited

U.S. PATENT DOCUMENTS

| | | | | |
|---|---|---|---|---|
| 7,282,723 B2* | 10/2007 | Schomacker | A61B 1/0655 | 600/478 |
| 7,309,867 B2* | 12/2007 | Costa | G01N 21/31 | 250/461.1 |
| 7,459,696 B2* | 12/2008 | Schomacker | A61B 5/7203 | 250/458.1 |
| 7,469,160 B2* | 12/2008 | Banks | G01N 21/31 | 600/125 |
| 7,817,835 B2 | 10/2010 | Fan et al. | | |
| 7,933,782 B2* | 4/2011 | Reiner | G16H 20/10 | 600/300 |
| 8,180,112 B2* | 5/2012 | Kurtz | G06V 40/50 | 382/116 |
| 8,412,544 B2* | 4/2013 | Reiner | G16H 30/40 | 600/300 |
| 8,867,822 B2* | 10/2014 | Oh | A61B 6/463 | 382/128 |
| 9,173,590 B2* | 11/2015 | Moats | G06T 7/0012 | |
| 9,401,020 B1* | 7/2016 | Li | G06V 20/647 | |
| 9,501,829 B2* | 11/2016 | Carlton | G16H 20/40 | |
| 9,691,167 B1 | 6/2017 | Frenkel et al. | | |
| 9,754,371 B2* | 9/2017 | Kateb | A61B 5/0042 | |
| 9,773,305 B2 | 9/2017 | Lee et al. | | |
| 10,368,809 B2 | 8/2019 | Kim et al. | | |
| 10,383,592 B2 | 8/2019 | Park | | |
| 10,420,530 B2* | 9/2019 | Hancock | A61B 8/467 | |
| 10,565,477 B2 | 2/2020 | Hsieh et al. | | |
| 10,699,410 B2* | 6/2020 | Pheiffer | G06T 7/136 | |
| 10,733,745 B2* | 8/2020 | Pizer | G06V 20/40 | |
| 10,776,456 B2* | 9/2020 | Mustakos | A61N 1/08 | |
| 10,810,736 B2* | 10/2020 | Fuchs | G06V 10/98 | |
| 10,825,180 B2* | 11/2020 | Chen | G06F 18/2321 | |
| 10,827,982 B2* | 11/2020 | Sitek | G06T 7/0012 | |
| 10,839,573 B2* | 11/2020 | Marino | G06Q 30/0276 | |
| 10,925,684 B2* | 2/2021 | Schwartz | A61B 34/10 | |
| 10,937,542 B1* | 3/2021 | Yildirim | G06T 7/11 | |
| 10,973,486 B2* | 4/2021 | Sjöstrand | A61K 51/0478 | |
| 11,069,056 B2* | 7/2021 | Perrin | G01N 33/57434 | |
| 11,170,508 B2* | 11/2021 | Avital | A61B 5/0042 | |
| 11,210,786 B2* | 12/2021 | Min | A61B 8/14 | |
| 11,227,390 B2* | 1/2022 | Huo | G16H 10/60 | |
| 11,227,683 B2* | 1/2022 | Morard | G06T 7/0014 | |
| 11,232,564 B2* | 1/2022 | Min | G06F 18/10 | |
| 11,232,569 B2* | 1/2022 | de Vaan | G06T 7/38 | |
| 11,250,944 B2* | 2/2022 | Adiri | G01N 33/52 | |
| 11,253,225 B2* | 2/2022 | Hancock | G01S 7/52082 | |
| 11,257,240 B2* | 2/2022 | Chaudhury | G06V 10/82 | |
| 11,276,170 B2* | 3/2022 | Min | G06F 18/2413 | |
| 11,282,170 B2* | 3/2022 | Gauriau | G06T 3/4061 | |
| 11,288,799 B2* | 3/2022 | Min | G06V 40/14 | |
| 11,302,001 B2* | 4/2022 | Min | G06T 7/0012 | |
| 11,315,247 B2* | 4/2022 | Min | A61B 8/14 | |
| 11,321,844 B2* | 5/2022 | Johnsson | G06T 7/10 | |
| 11,331,151 B2* | 5/2022 | Mahfouz | A61B 34/20 | |
| 11,344,374 B2* | 5/2022 | Tekiela | A61B 34/25 | |
| 11,348,257 B2* | 5/2022 | Lang | A61B 90/92 | |
| 11,367,190 B2* | 6/2022 | Min | A61K 49/04 | |
| 11,386,988 B2* | 7/2022 | Johnsson | G16H 50/20 | |
| 11,410,353 B2* | 8/2022 | Helle | G06T 5/50 | |
| 11,412,917 B2* | 8/2022 | Oosake | A61B 1/0005 | |
| 11,416,798 B2* | 8/2022 | Brannon | G06Q 30/018 | |
| 11,452,871 B2* | 9/2022 | McIntyre | A61N 1/0529 | |
| 11,529,110 B2* | 12/2022 | Taubmann | G16H 40/60 | |
| 11,537,952 B2* | 12/2022 | Avare | G06N 20/00 | |
| 11,538,155 B2* | 12/2022 | Fuchs | G16H 50/70 | |
| 11,544,851 B2* | 1/2023 | Wainrib | G06T 7/11 | |
| 11,546,690 B2* | 1/2023 | Wexler | H04R 5/04 | |
| 11,551,353 B2* | 1/2023 | Golden | G06N 3/08 | |
| 11,557,036 B2* | 1/2023 | Liao | A61B 5/7267 | |
| 11,564,621 B2* | 1/2023 | Anand | G06T 7/0012 | |
| 11,576,677 B2* | 2/2023 | Shelton, IV | A61M 1/73 | |
| 11,583,346 B2* | 2/2023 | Bort | A61B 34/20 | |
| 11,593,940 B2* | 2/2023 | Khademi | A61B 5/055 | |
| 11,596,316 B2* | 3/2023 | Tran | G05B 13/042 | |
| 11,612,444 B2* | 3/2023 | Shelton, IV | A61B 18/1206 | 606/205 |
| 11,615,535 B2* | 3/2023 | Huo | G16H 10/60 | 382/131 |
| 11,627,864 B2* | 4/2023 | Yumbe | A61B 1/000094 | 348/68 |
| 11,636,171 B2* | 4/2023 | Brannon | G06F 16/951 | 715/234 |
| 11,640,661 B2* | 5/2023 | Washko, Jr. | G06V 10/40 | 382/131 |
| 11,651,402 B2* | 5/2023 | Barday | G06Q 10/063114 | 705/325 |
| 11,657,508 B2* | 5/2023 | Richter | G06V 30/2504 | 600/425 |
| 11,657,531 B1* | 5/2023 | Ebrahimi Afrouzi | G01S 17/48 | 382/284 |
| 11,665,284 B2* | 5/2023 | Jorasch | H04N 7/147 | 709/204 |
| 11,676,705 B2* | 6/2023 | Adiri | G06T 7/0012 | 382/128 |
| 11,676,719 B2* | 6/2023 | Feczko | G16H 20/70 | 706/12 |
| 11,682,186 B2* | 6/2023 | Fuchs | G06V 10/82 | 382/128 |
| 11,690,586 B2* | 7/2023 | Min | G06V 40/14 | 600/300 |
| 11,699,236 B2* | 7/2023 | Avital | G01R 33/5608 | 382/131 |
| 11,705,226 B2* | 7/2023 | Colley | G16H 50/70 | 705/3 |
| 11,727,547 B2* | 8/2023 | Adiri | G06V 10/56 | 382/128 |
| 11,727,581 B2* | 8/2023 | Lang | A61F 2/4684 | 345/8 |
| 11,741,605 B2* | 8/2023 | Liao | A61B 5/7267 | |
| 11,751,826 B2* | 9/2023 | Min | G06V 10/764 | 600/300 |
| 11,766,229 B2* | 9/2023 | Min | A61B 8/5223 | 382/131 |
| 11,766,230 B2* | 9/2023 | Min | A61B 8/5223 | 382/131 |
| 11,779,292 B2* | 10/2023 | Min | A61B 6/481 | 600/300 |
| 11,783,484 B2* | 10/2023 | Mostapha | G16H 50/20 | |
| 11,783,485 B2* | 10/2023 | Mostapha | G06N 20/00 | |
| 2003/0013951 A1* | 1/2003 | Stefanescu | G06F 16/5838 | 600/407 |
| 2017/0278289 A1* | 9/2017 | Marino | G06T 7/536 | |
| 2017/0337687 A1* | 11/2017 | Wang | G06T 7/11 | |
| 2019/0369191 A1 | 12/2019 | Gong et al. | | |
| 2020/0020079 A1* | 1/2020 | Gauriau | G06T 17/00 | |
| 2020/0082531 A1* | 3/2020 | de Vaan | G06T 7/62 | |
| 2020/0085382 A1* | 3/2020 | Taerum | G06T 7/0016 | |
| 2020/0219272 A1* | 7/2020 | Pizer | G06V 20/40 | |
| 2020/0258227 A1* | 8/2020 | Liao | G06T 7/30 | |
| 2020/0294284 A1 | 9/2020 | Adler et al. | | |
| 2020/0311490 A1 | 10/2020 | Lee et al. | | |
| 2020/0335201 A1 | 10/2020 | Ionasec et al. | | |
| 2020/0342600 A1* | 10/2020 | Sjöstrand | A61B 6/032 | |
| 2020/0357120 A1* | 11/2020 | Kang | A61B 5/0042 | |
| 2021/0158523 A1* | 5/2021 | Khademi | G16H 30/40 | |
| 2021/0369195 A1* | 12/2021 | Russakoff | G16H 30/40 | |
| 2022/0012892 A1* | 1/2022 | Avital | A61B 5/4381 | |
| 2022/0020147 A1* | 1/2022 | Sasada | G06T 11/00 | |
| 2022/0087651 A1* | 3/2022 | Alizad | A61B 8/0891 | |
| 2022/0148174 A1* | 5/2022 | de Vaan | G06T 7/246 | |
| 2022/0245810 A1* | 8/2022 | Yao | G06V 10/82 | |
| 2022/0254023 A1* | 8/2022 | Mckinney | G06F 18/24133 | |
| 2022/0284578 A1* | 9/2022 | Patil | G06T 7/11 | |
| 2022/0296313 A1* | 9/2022 | Mahfouz | A61B 6/487 | |
| 2023/0082710 A1* | 3/2023 | Fuchs | G06F 18/2113 | 382/128 |
| 2023/0083657 A1* | 3/2023 | Wang | G16H 30/20 | 382/128 |
| 2023/0097224 A1* | 3/2023 | Genghi | G16H 30/40 | 382/128 |

(56) References Cited

U.S. PATENT DOCUMENTS

| | | | | |
|---|---|---|---|---|
| 2023/0106440 A1* | 4/2023 | Golden | G06V 10/82 | 382/131 |
| 2023/0114934 A1* | 4/2023 | Liao | A61B 5/7267 | 382/128 |
| 2023/0115732 A1* | 4/2023 | Brynolfsson | G06T 7/0012 | 382/128 |
| 2023/0148980 A1* | 5/2023 | Sjöstrand | G06T 7/0014 | 600/431 |
| 2023/0157756 A1* | 5/2023 | Simoes | G16H 50/50 | 703/11 |
| 2023/0190390 A1* | 6/2023 | Shelton, IV | A61B 34/25 | 606/205 |
| 2023/0215004 A1* | 7/2023 | Washko, Jr. | G06T 7/0012 | 600/300 |
| 2023/0226696 A1* | 7/2023 | Mandlekar | B25J 13/006 | 700/264 |
| 2023/0254412 A1* | 8/2023 | Jorasch | H04L 65/1069 | 709/204 |
| 2023/0259852 A1* | 8/2023 | Marx | G06F 40/284 | 705/2 |
| 2023/0274439 A1* | 8/2023 | Preuhs | G06T 7/0016 | 382/128 |
| 2023/0298306 A1* | 9/2023 | Baras | G06V 10/74 | 382/128 |
| 2023/0343455 A1* | 10/2023 | Kwon | G06T 7/0012 | |

FOREIGN PATENT DOCUMENTS

| | | |
|---|---|---|
| KR | 10-2014-0091176 A | 7/2014 |
| KR | 10-2016-0012758 A | 2/2016 |
| KR | 10-1910822 B1 | 10/2018 |
| KR | 10-1923962 B1 | 11/2018 |
| KR | 10-2019-0002960 A | 1/2019 |
| KR | 10-1943011 B1 | 1/2019 |
| KR | 10-2070427 B1 | 1/2020 |

* cited by examiner

MEDICAL IMAGE READING ASSISTANT APPARATUS AND METHOD FOR ADJUSTING THRESHOLD OF DIAGNOSTIC ASSISTANT INFORMATION BASED ON FOLLOW-UP EXAMINATION

CROSS-REFERENCE TO RELATED APPLICATION

This application claims priority to Korean Patent Application No. 10-2020-0164594 filed on Nov. 30, 2020, which is incorporated herein by reference in its entirety.

TECHNICAL FIELD

The present invention relates to an apparatus and method that assist the reading of a medical image of a subject. More particularly, the present invention relates to a computing system that assists the reading of a medical image using an analysis result of a medical artificial neural network, and software that is executed in the computing system.

RELATED ART

Currently, medical images such as computed tomography (CT) images are widely used to analyze lesions and use analysis results for diagnosis. For example, chest CT images are frequently used for reading because they allow readers to observe abnormalities in parts of the human body such as the lungs, the bronchi, and the heart.

Some of the findings that can be read through chest CT images may be easily overlooked by human doctors because they are not easy to read and even radiologists can distinguish their features and forms only after years of training. In particular, when the level of difficulty in reading is high as in the reading of a lung nodule, the case of overlooking a lesion may occur even when a doctor pays a high degree of attention, which may lead to trouble.

In order to assist the reading of images that may be easily overlooked by humans, the need for computer-aided diagnosis (CAD) has arisen. Conventional CAD technology is limited to assisting doctors in making decisions in significantly limited areas. For example, Korean Patent Application Publication No. 10-2014-0091176 and U.S. Pat. No. 9,773,305 disclose a conventional apparatus and method for assisting the diagnosis of lesions.

The reading of a lesion using CAD may include the process of identifying a suspected lesion first and then evaluating a score (e.g., confidence, malignity, or the like) for that region. For example, if a plurality of nodules is found in the lungs, it will be necessary to specify a nodule that is expected to have the highest malignity and to determine a future treatment plan.

Meanwhile, since there is a plurality of nodules, it is not known until reading which of the nodules is most malignant. Accordingly, there frequently occurs a case where diagnosis is performed from a nodule whose actual malignity is not high or which is not expected to be highly malignant and thus the efficiency of reading is degraded. It is also difficult to know which nodule is a real nodule before reading and reliability is low. Accordingly, when the diagnosis is performed from a portion that is not expected to be an actual nodule, the efficiency of reading is also deteriorated.

Korean Patent No. 10-1943011 entitled "Method for Assisting Reading of Medical Image of Subject and Apparatus using Same" proposes a method that introduces a scheme for allocating scores for confidence and/or malignity to lesions detected in a conventional lesion detection system and allows a lesion having a higher score for confidence and/or malignity among the detected lesions to be read first, thereby increasing the efficiency of reading, and also proposes an apparatus using the same.

Korean Patent No. 10-1943011 discloses a configuration in which when a number of lesions are detected for a single type of disease, a list in which entries are arranged from a lesion having the highest score for confidence and/or malignity within a single display setting is displayed, and an image related to a selected lesion is displayed when a user selects the lesion from the list. According to Korean Patent No. 10-1943011, the scores of lesions are filtered based on a predetermined threshold and only lesions having a score equal to or larger than the threshold are displayed, so that assistance is provided to increase the efficiency of the reading task of a medical member in charge.

Meanwhile, as another related art, Korean Patent No. 10-1923962 entitled "Method for Assisting Reading of Medical Images and Apparatus Using Same" discloses an invention that assists the easy reading of chest CT images in time series, and provides assistance so that comparison and analysis are facilitated by displaying a time series set of medical images at the same visual locations using follow-up examination.

SUMMARY

As to recent medical images such as CT or magnetic resonance imaging (MRI) images, a series of medical images is acquired through a single acquisition process, and the series of medical images is not limited to a single type of lesion but may also be used to detect various types of lesions. For example, for the lungs, a lung nodule as well as chronic obstructive pulmonary disease (COPD) may be diagnosed, emphysema may be diagnosed, and/or chronic bronchitis and/or an airway-related disease may also be diagnosed. In addition, coronary artery calcification (CAC) scoring may be analyzed in a chest CT image in addition to lung disease.

In the aforementioned related art documents, i.e., Korean Patent Application Publication No. 10-2014-0091176 entitled "Apparatus and Method for Diagnosing Lesions," U.S. Pat. No. 9,773,305 entitled "Lesion Diagnosis Apparatus and Method," Korean Patent No. 10-1943011 entitled "Method for Assisting Reading of Medical Image of Subject and Apparatus Using Same," and Korean Patent No. 10-1923962 entitled "Method for Assisting Reading of Medical images and Apparatus Using Same," lesion candidates are detected and classified and also findings are generated using an artificial neural network. Each of the findings includes diagnostic assistant information, and the diagnostic assistant information may include a probability that each finding is actually a lesion, confidence in the finding, malignity, and quantitative measurements of the sizes and volumes of lesion candidates corresponding to the finding.

In medical image reading assistance using an artificial neural network, each finding must include diagnostic assistant information obtained by quantifying probability or confidence. Since it is not possible to provide all the findings to a user, the findings are filtered by applying a predetermined threshold, and only passed findings are provided to the user.

Although a user menu via which a user can adjust a threshold is disclosed in the related art document, i.e., Korean Patent No. 10-1943011 entitled "Method for Assisting Reading of Medical Image of Subject and Apparatus Using Same," the same threshold is applied to all lesions or findings in a uniform manner in other related arts.

When different thresholds are applied to lesions or findings by taking into consideration clinical context, a user can focus on clinically significant findings. The present invention is a technology that assists the reading of medical images, and an object of the present invention is to provide a user interface that analyzes the correlation between finding's information about a past medical image and finding's information about a current medical image based on follow-up information and applies a different threshold of diagnostic assistant information to a lesion or finding of the current medical image present at the same location as the corresponding lesion or finding of the past medical image, thereby allowing a user to focus more on the clinically significant finding.

Another object of the present invention is to provide a user interface that recognizes contextual information related to follow-up information when the magnitude of finding's information about a current medical image becomes larger than that of corresponding finding's information about a past medical image, the probability of being a lesion increases, or the possibility of malignity increases based on the follow-up information and applies a different threshold of diagnostic assistant information based on the contextual information, thereby allowing a user to focus more on the clinically significant finding.

Another object of the present invention is to provide a user interface that provides a finding having special clinical significance with a visualization element distinct from those of the rest of the findings during the above process, thereby allowing the user to focus on the clinically significant finding.

According to an aspect of the present invention, there is provided a medical image reading assistant apparatus for assisting the reading of a medical image. The medical image reading assistant apparatus includes a computing system. The computing system includes: a receiver interface configured to receive a first medical image included in a time series set of medical images and a second medical image following the first medical image; and at least one processor configured to: generate follow-up information between first findings on the first medical image and second findings on the second medical image by comparing the locations of the first findings and the locations of the second findings; select at least some of the first findings as first valid findings to be provided to a user based on a first threshold of diagnostic assistant information for each of the first findings; set a second threshold of diagnostic assistant information for each of the second findings based on the follow-up information; and select at least some of the second findings as second valid findings to be provided to the user based on the second threshold. In this case, the at least one processor provides the first valid findings and the second valid findings to the user via a user interface.

The at least one processor may be further configured to select a first subset of second findings, corresponding to the first findings among the second findings on the second medical image, as the second valid findings by applying the second threshold to the first subset of second findings based on the follow-up information. In this case, the at least one processor may select a second subset of second findings, not corresponding to the first findings among the second findings on the second medical image, as third valid findings by applying the first threshold value to the second subset of second findings.

The at least one processor may be further configured to select a third subset, including second findings within the first subset having diagnostic assistant information greater than the diagnostic assistant information of the first findings corresponding to the second findings within the first subset, as fourth valid findings by applying a third threshold smaller than the second threshold to the third subset based on the follow-up information.

The at least one processor may be further configured to select a fourth subset of first findings, not included in the first valid findings and corresponding to the second valid findings among the first findings on the first medical image, as fifth valid findings.

The computing system may further include a first artificial neural network that has learned the function of generating the follow-up information between the first findings and the second findings. In this case, the at least one processor may be further configured to control the first artificial neural network so that the first artificial neural network can identify a first subset of second findings corresponding to the first findings among the second findings on the second medical image.

The computing system may further include a second artificial neural network that has learned the function of detecting the first findings on the first medical image and the second findings on the second medical image. In this case, the at least one processor may be further configured to control the second artificial neural network so that the second artificial neural network can detect the first findings on the first medical image and the second findings on the second medical image.

The at least one processor may be further configured to receive the first findings on the first medical image together with the first medical image and the second findings on the second medical image together with the second medical image via the receiver interface.

The at least one processor may be further configured to, in the case where a first valid finding displayed on the first medical image and a second valid finding displayed on the second medical image via the user interface correspond to each other based on the follow-up information, when any one of the first and second valid findings corresponding to each other is selected and visually activated, also visually activate the other one.

According to another aspect of the present invention, there is provided a medical image reading assistant method for assisting the reading of a medical image. The medical image reading assistant method is executed by a computing system, and the computing system includes at least one processor. The medical image reading assistant method includes: receiving, by the at least one processor, a first medical image included in a time series set of medical images and a second medical image following the first medical image via a receiver interface; generating, by the at least one processor, follow-up information between first findings on the first medical image and second findings on the second medical image by comparing the locations of the first findings and the locations of the second findings; selecting, by the at least one processor, at least some of the first findings as first valid findings to be provided to a user based on a first threshold of diagnostic assistant information for each of the first findings; setting, by the at least one processor, a second threshold of diagnostic assistant information for each of the second findings based on the follow-up information, and selecting, by the at least one processor, at least some of the second findings as second valid findings to be provided to the user based on the second threshold; and providing, by the at least one processor, the first valid findings and the second valid findings to the user via a user interface.

The selecting at least some of the second findings as second valid findings may include selecting, by the at least one processor, a first subset of second findings, corresponding to the first findings among the second findings on the second medical image, as the second valid findings by applying the second threshold to the first subset of second findings based on the follow-up information. In this case, the medical image reading assistant method may further include: selecting, by the at least one processor, a second subset of second findings, not corresponding to the first findings among the second findings on the second medical image, as third valid findings by applying the first threshold value to the second subset of second findings;

and providing, by the at least one processor, the third valid findings, together with a visualization element distinct from those of the first and second valid findings, to the user via the user interface.

The medical image reading assistant method may further include: selecting, by the at least one processor, a third subset, including second findings within the first subset having diagnostic assistant information greater than diagnostic assistant information of the first findings corresponding to the second findings within the first subset, as fourth valid findings by applying a third threshold smaller than the second threshold to the third subset based on the follow-up information; and providing, by the at least one processor, the fourth valid findings, together with a visualization element distinct from those of the first to third valid findings, to the user via the user interface.

The medical image reading assistant method may further include: selecting, by the at least one processor, a fourth subset of first findings, not included in the first valid findings and corresponding to the second valid findings among the first findings on the first medical image, as fifth valid findings; and providing, by the at least one processor, the fifth valid findings, together with a visualization element distinct from those of the first to third valid findings, to the user via the user interface.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION

Other objects and features of the present invention in addition to the above-described objects will be apparent from the following description of embodiments to be given with reference to the accompanying drawings.

Embodiments of the present invention will be described in detail below with reference to the accompanying drawings. In the following description, when it is determined that a detailed description of a related known component or function may unnecessarily make the gist of the present invention obscure, it will be omitted.

Deep learning/CNN-based artificial neural network technology, which has recently developed rapidly, is considered for the purpose of identifying a visual element that is difficult to identify with the human eye when it is applied to the field of imaging. The fields of application of the above technology are expected to expand to various fields such as security, medical imaging, and non-destructive testing.

For example, in the field of medical imaging, there are cases where a tissue in question is not immediately diagnosed as a cancer tissue in a biopsy state but whether it is a cancer tissue is determined only after being monitored from a pathological point of view. Although it is difficult to confirm whether a corresponding cell is a cancer tissue in a medical image with the human eye, there is an expectation that the application of artificial neural network technology may acquire more accurate prediction results than observation with the human eye.

It is expected that this artificial neural network technology is applied to and performs the analysis process of detecting a disease or lesion that is difficult to identify with the human eye in a medical image, segmenting a region of interest such as a specific tissue, and measuring the segmented region.

The items known to those skilled in the art prior to the filing of the present application among the configuration of the present invention will be described as parts of the configuration of the present invention therein as necessary. However, when it is determined that the items obvious to those skilled in the art may make the gist of the invention obscure, descriptions thereof may be omitted. In addition, descriptions of the items omitted herein may be substituted by providing notification that they are known to those skilled in the art via the related art documents cited herein, e.g., Korean Patent Application Publication No. 10-2014-0091176 entitled "Apparatus and Method for Diagnosing Lesions," U.S. Pat. No. 9,773,305 entitled "Lesion Diagnosis Apparatus and Method," Korean Patent No. 10-1943011 entitled "Method for Assisting Reading of Medical Image of Subject and Apparatus Using Same," and Korean Patent No. 10-1923962 entitled "Method for Assisting Reading of Medical images and Apparatus Using Same."

In the aforementioned related art documents, lesion candidates are detected and classified and also findings are generated using an artificial neural network. Each of the findings includes diagnostic assistant information, and the diagnostic assistant information may include a probability that each finding is actually a lesion, confidence in the finding, malignity, and quantitative measurements of the sizes and volumes of lesion candidates corresponding to the finding.

In medical image reading assistance using an artificial neural network, each finding must include diagnostic assistant information obtained by quantifying probability or confidence. Since it is not possible to provide all the findings to a user, the findings are filtered by applying a predetermined threshold, and only passed findings are provided to a user.

Although a user menu via which a user can adjust a threshold is disclosed in the related art document, i.e., Korean Patent No. 10-1943011 entitled "Method for Assisting Reading of Medical Image of Subject and Apparatus Using Same," the same threshold is applied to all lesions or findings in a uniform manner in other related arts.

Some of the items disclosed in these related art documents are related to the objects to be solved by the present invention, and some of the solutions adopted by the present invention are also applied to these related art documents.

In the following description to be given in conjunction with FIGS. 1 to 6, descriptions of the items considered to be well-known techniques that are widely known in the technical field of the present invention may be omitted as necessary in order to prevent the gist of the present invention from being obscured, or may be substituted by citing related art documents.

In addition, some or all of the configurations of the related art documents cited above and related art documents to be cited later may be related to some of the objects to be achieved by the present invention, and some of the solutions adopted by the present invention may be borrowed from the related art documents.

Only the items also included in order to embody the present invention among those disclosed in the related art documents will be considered to be parts of the configuration of the present invention.

Details of the present invention will be described below with reference to the embodiments of FIGS. 1 to 6.

Figure 1:
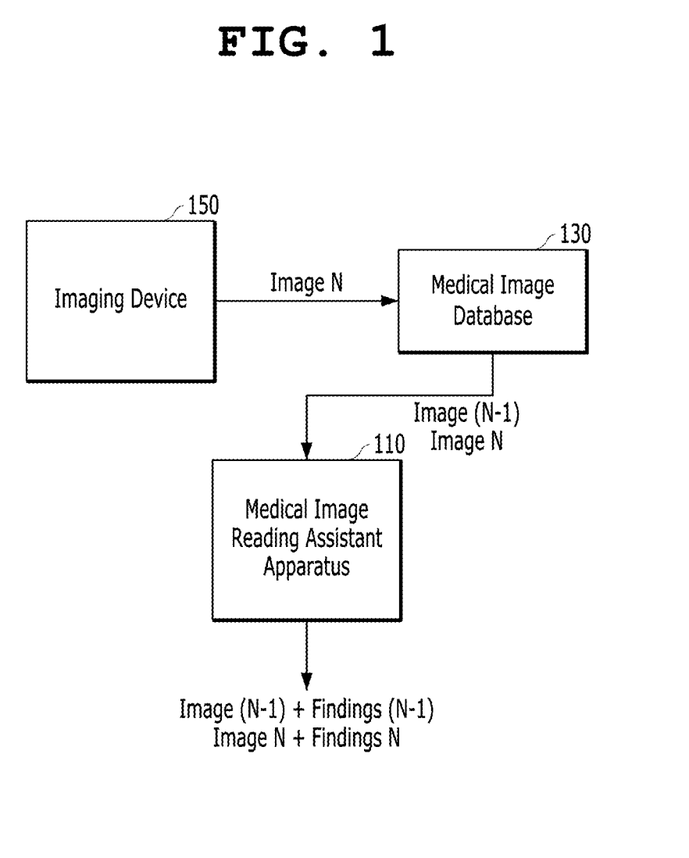
FIG. 1 is a diagram showing a medical image reading workflow executed in a system including a medical image reading assistant apparatus according to an embodiment of the present invention.

FIG. 1 is a diagram showing a medical image reading workflow executed in a system including a medical image reading assistant apparatus 110 according to an embodiment of the present invention.

The medical image reading assistant apparatus 110 according to the present embodiment receives a first medical image N-1 and a second medical image N included in a time series set of medical images from a medical image database 130 in order to assist the reading of a medical image. In this case, a medical imaging device 150 newly generates a second medical image related to a lesion/diagnosis to be diagnosed. The second medical image generated by the medical imaging device 150 is stored in the medical image database 130, and may be transferred from the medical image database 130 to the medical image reading assistant apparatus 110 in response to an invocation from the medical image reading assistant apparatus 110. The medical image database 130 receives the second medical image from the medical imaging device 150, searches for a first medical image acquired by photographing the same object as the second medical image, and transfers the first medical image and the second medical image together to the medical image reading assistant apparatus 110. In this case, the medical image database 130 may be a picture archive communication system (PACS).

The medical image reading assistant apparatus 110 selects first findings having diagnostic assistant information equal to or larger than a first threshold from among first findings on the first medical image as first valid findings by filtering the first findings on the first medical image based on the first threshold, and provides the selected first findings, together with the first medical image, to a user. In addition, the medical image reading assistant apparatus 110 selects second valid findings by setting a second threshold smaller than the first threshold for second findings corresponding to the first findings based on follow-up information from among second findings on the second medical image and then filtering the second findings corresponding to the first findings based on the second threshold, and provides the selected second findings, together with the second medical image, to a user. The medical image reading assistant apparatus 110 may generate third valid findings by applying the first threshold to second findings not corresponding to the first findings based on the follow-up information among the second findings on the second medical image. These third valid findings may be provided to the user together with the second medical image. Among the first valid findings on the first medical image, a subset corresponding to the second valid findings and the remaining subset not corresponding to the second valid findings may be visualized with distinct visualization elements. The second valid findings on the second medical image may be visualized with a visualization element distinct from that of the third valid findings.

Figure 2:
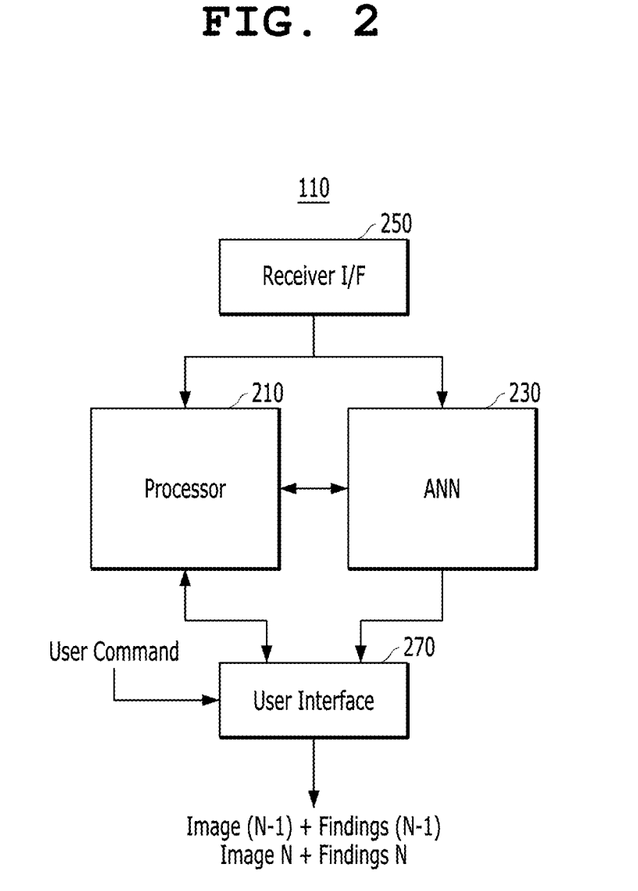
FIG. 2 is a block diagram showing an embodiment of the medical image reading assistant apparatus of FIG. 1.

FIG. 2 is a block diagram showing an embodiment of the medical image reading assistant apparatus 110 of FIG. 1.

Referring to FIG. 2, the medical image reading assistant apparatus 110 according to the present embodiment may include a computing system (not shown). The computing system included in the medical image reading assistant apparatus 110 may include a receiver interface 250, at least one processor 210, and a first artificial neural network 230. The medical image reading assistant apparatus 110 may further include a user interface 270. Although not shown in FIG. 2, the medical image reading assistant apparatus 110 may further include a transmission interface configured to transmit data to the outside. The user interface 270 may include a display, a touch screen, a keyboard, a mouse, a trackball, a virtual keyboard, and so on.

Referring to FIGS. 1 and 2 together, the receiver interface 250 may receive the first medical image included in a time series set of medical images and the second medical image following the first medical image from the medical image database 130.

The at least one processor 210 may generate the follow-up information between first findings on the first medical image and second findings on the second medical image by comparing the locations of the first findings and the locations of the second findings. In this case, the at least one processor 210 may include the first artificial neural network 230 so that the first artificial neural network 230 can infer whether the first findings and the second findings are follow-up matched with each other. In other words, the at least one processor 210 may control the first artificial neural network 230 so that the first artificial neural network 230 identifies a first subset of second findings corresponding to the first findings among the second findings on the second medical image.

Each finding includes diagnostic assistant information. The diagnostic assistant information may include a probability that each finding is actually a lesion, confidence in the finding, malignity, and quantitative measurements of the size and volume of each lesion candidate corresponding to the finding.

The at least one processor 210 may select at least some of the first findings as first valid findings to be provided to the user based on the first threshold of diagnostic assistant information for each of the first findings, and may set the second threshold of the diagnostic assistant information for each of the second findings based on the follow-up information.

The at least one processor 210 may select at least some of the second findings as the second valid findings to be provided to the user based on the second threshold. In this case, the at least one processor 210 provides the first valid findings and the second valid findings to the user via the user interface 270.

The at least one processor 210 may set different thresholds for follow-up matched second findings and non-follow-up matched second findings among the second findings.

The at least one processor 210 may select a first subset of the second findings as second valid findings by applying the second threshold to the first subset of the second findings corresponding to the first findings among the second findings based on the follow-up information. In this case, the at least one processor 210 may select a second subset of the second findings as third valid findings by applying the first threshold to the second subset of second findings not corresponding to the first findings among the second findings. Findings included in the first subset of the second findings are considered as follow-up matched second findings since they are found in both of the first medical image and the second medical image. Findings included in the second subset of the second findings are considered as new (non-follow-up matched) second findings found only in the second medical image. The first threshold (loose threshold for new findings) is applied to the second subset and the second threshold (strict threshold for follow-up matched findings) is applied to the first subset.

The at least one processor 210 may provide the third valid findings, together with a visualization element distinct from those of the first and second valid findings, to the user via the user interface 270. The first valid findings may be displayed on the first medical image, and the second valid findings and the third valid findings may be displayed on the second medical image.

For findings having special clinical significance, e.g., for findings in which a measured size is increased or the probability of being a lesion is increased, among the follow-up matched ones of the second findings, the third threshold adjusted to a lower value than the second threshold may be applied.

The at least one processor 210 may select a third subset as fourth valid findings by applying the third threshold smaller (in other words, stricter) than the second threshold to the third subset formed to include second findings, having diagnostic assistant information greater than diagnostic assistant information of the first findings corresponding to the second findings within the first subset, among the second findings within the first subset based on the follow-up information. It means, the fourth valid findings are findings need to be monitored more carefully, the third threshold (stricter threshold) is applied to the fourth valid findings.

The diagnostic assistant information may include at least one of a probability that a corresponding finding is a lesion, a possibility of malignity, confidence in the finding, and a quantitative measurement of the size or volume of a lesion corresponding to the corresponding finding. Furthermore, the diagnostic assistant information may be represented by a single index by allocating a weight to each of one or more of the probability that the corresponding finding is a lesion, the possibility of malignity, the confidence in the finding, and the quantitative measurement of the size or volume of the lesion corresponding to the finding and then summing the weighted values. In this case, the index may be treated as a score, and may be used as a representative value representing the diagnostic assistant information. In this case, all the first to third thresholds may be applied to the representative score of diagnostic assistant information.

According to another embodiment of the present invention, the first to third thresholds may not be applied to only one representative value parameter, but may be applied to each of the parameters constituting the diagnostic assistant information. In this case, a first threshold set may be applied to each of the parameters, or a second threshold set may be applied to each of the parameters of the diagnostic assistant information.

For example, a first finding found in a past medical image may be classified as a first valid finding when the score of the diagnostic assistant information is 90 points or more. A second finding newly found in a current medical image may also be classified as a third valid finding when the score of the diagnostic assistant information is 90 points or more. However, a second finding that is follow-up matched with the first finding of the past medical image and that is also present in the current medical image requires more clinical attention, so that it may be classified as a second valid finding when the score of the diagnostic assistant information is 80 points or more.

When all the second findings are not classified as the second valid finding or the third valid finding, there may be findings that are follow-up matched with the first findings which are not included in the first valid findings since they have smaller diagnosis assistant information than the first threshold. In a combination of first and second findings corresponding to each other, the first finding may have been evaluated as 50 points in a past medical image, whereas the second finding may be evaluated as 70 points in a current medical image. Although this case is not a significant problem now, attention is required in the future, and thus the case having 70 points or more may be classified as a fourth valid finding. In this case, in the relationship between the first and second findings corresponding to each other, when the representative value of the diagnostic assistant information of the second finding is increased by a reference value (e.g., +15 points) or more compared to the representative value of the diagnostic assistant information of the first finding, a third threshold (e.g., 70 points) may be applied. In other words, when a first finding is not included in the first valid findings since it has smaller diagnostic assistant information than the first threshold and a second finding corresponding to it has greater diagnostic assistant information than the specific threshold, a pair of the first finding and the corresponding second finding needs to be monitored for future disease problem. In this case the corresponding second finding is filtered by one of the first threshold, the second threshold, and the third threshold. Otherwise, the corresponding second finding is filtered by increment in the diagnosis assistant information with a certain degree. This threshold or filtering by increment with the certain degree can be called an adjusted second threshold.

The at least one processor 210 may further include the step of providing the fourth valid findings, together with a visualization element (for example, color, shape, mark, or the like) distinct from those of the first to third valid findings, to the user via the user interface 270.

Even when first findings are smaller than the original first threshold but the second findings corresponding to the first findings are equal to or larger than the adjusted second threshold, among the first findings on the first medical image, the first findings may be denoted by a different visual element (for example, color, shape, mark, or the like). The at least one processor 210 may select a fourth subset of first findings, corresponding to the second valid findings without being included in the first valid findings among the first findings on the first medical image, as fifth valid findings. The at least one processor 210 may provide the fifth valid findings, together with a visualization element distinct from those of the first to third valid findings, to the user via the user interface 270.

In the foregoing example, a first finding is recognized as a first valid finding only when it has 90 points or more, but first findings corresponding to the findings classified as a second valid finding and/or a fourth valid finding among the second findings may be present in the past medical image. In this case, the first findings corresponding to the second findings classified as the second valid finding and/or the fourth valid finding may be selected as fifth valid findings, may be visually distinguished from other valid findings, and may be provided to the user.

According to an embodiment of the present invention, the computing system in the medical image reading assistant apparatus 110 may further include an artificial neural network engine configured to have the function of detecting findings. For example, the computing system may further include a second artificial neural network (not shown) that has learned the function of detecting first findings for a first medical image and detecting second findings for a second medical image. In this case, the at least one processor 210 may control the second artificial neural network to detect the first findings on the first medical image and the second findings on the second medical image.

According to an embodiment of the present invention, a function for cross link between the first findings and the second findings may be provided to the user via the user interface 270. For example, in the case where the first valid finding displayed on the first medical image and the second valid finding displayed on the second medical image correspond to each other based on the follow-up information, when any one of first and second valid findings corresponding to each other is selected and visually activated (marked and/or emphasized from other first and second valid findings), the least one processor 210 may also visually activate the other one corresponding to the visually activated one through the user interface 270.

According to an embodiment of the present invention, there may be provided a user interface 270 configured to analyze the correlation between finding's information (for example, diagnosis assistant information) about a past medical image and finding's information about a current medical image based on follow-up information and to apply a different threshold of diagnostic assistant information to a lesion or finding of the current medical image present at the same location as the corresponding lesion or finding of the past medical image, thereby allowing a user to focus more on the clinically significant finding.

According to an embodiment of the present invention, there may be provided a user interface 270 configured to recognize contextual information related to follow-up information when the magnitude of finding's information about a current medical image becomes larger than that of corresponding finding's information about a past medical image, the probability of being a lesion increases, or the possibility of malignity increases based on the follow-up information and to apply a different threshold of diagnostic assistant information again based on the contextual information related to the follow-up information, thereby allowing a user to focus more on the clinically significant finding.

According to an embodiment of the present invention, there may be provided a user interface 270 configured to provide a finding having special clinical significance with a visualization element distinct from those of the rest of the findings, thereby allowing a user to focus more on the clinically significant finding.

In this case, although the user may be a medical professional such as a clinician or a radiologist, the user may be an assistant staff member having only knowledge sufficient to check whether basic preprocessing such as image segmentation has been performed reasonably and/or appropriately depending on an object to be diagnosed. In other words, a person may be included in the user meant in the present invention as long as not only the person does not have clinical knowledge but has a degree of representativeness sufficient to check whether main visual information for the diagnosis/analysis/measurement of a specific disease or lesion has been reasonably and appropriately represented to some degree.

Figure 3:
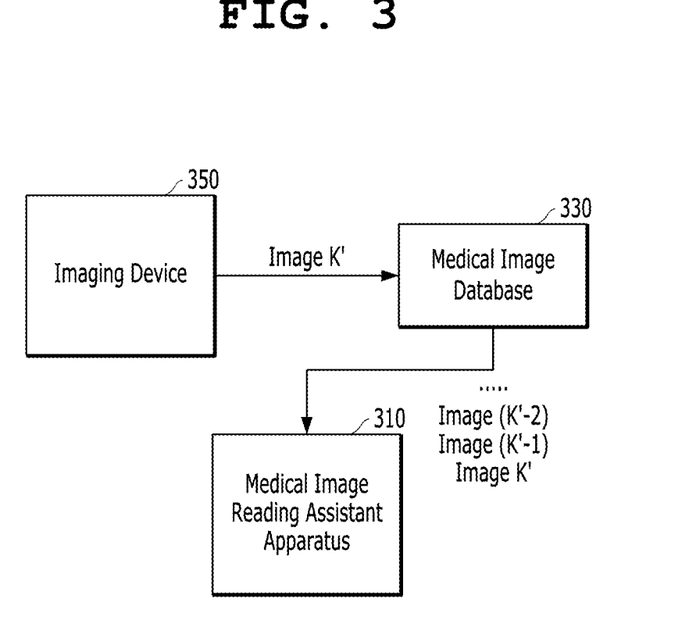
FIG. 3 is a diagram showing a training process in which the artificial neural network of a medical image reading assistant apparatus is trained according to an embodiment of the present invention.

FIG. 3 is a diagram showing a training process in which the artificial neural network of a medical image reading assistant apparatus 310 is trained according to an embodiment of the present invention.

A training dataset may be prepared as follows.

For example, when a medical imaging apparatus 350 generates a new medical image K' and transfers it to a medical image database 330, the medical image database 330 may generate a dataset including a plurality of past medical images (medical images (K'-1), (K'-2), . . . ) included in the same time series set as the medical image K' and the medical image K'. In this case, at least one of the medical image database 330 and the medical image reading assistant apparatus 310 may generate medical image combinations of paired images selected from among the plurality of medical images K', K'-1, K'-2, . . . . These medical image combinations constitute a training dataset that enables the learning of a follow-up function.

The medical image reading assistant apparatus 310 according to an embodiment of the present invention may receive an already paired instruction dataset, or may generate a training dataset of paired images after receiving the plurality of medical images K', K'-1, K'-2, . . . .

Figure 4:
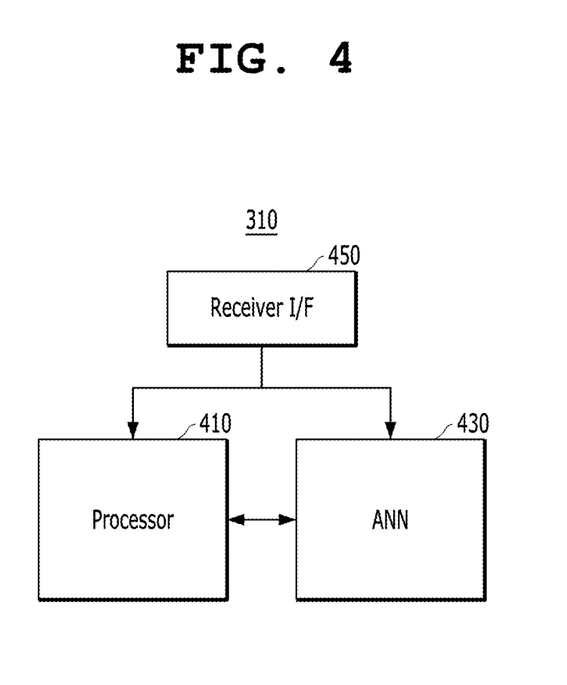
FIG. 4 is a block diagram showing the training/learning process of an artificial neural network executed inside the medical image reading assistant apparatus of FIG. 3.

FIG. 4 is a block diagram showing the training/learning process of an artificial neural network 430 executed inside the medical image reading assistant apparatus 310 of FIG. 3.

The medical image reading assistant apparatus 310 includes a receiver interface 450, at least one processor 410, and the artificial neural network 430.

The at least one processor 410 transfers a plurality of training datasets to the artificial neural network 430, and controls the artificial neural network 430 so that the artificial neural network 430 analyzes the locational correction between medical image pairs acquired by examining the same object but having different examination times and learns a follow-up matching function.

Meanwhile, in the embodiment of FIG. 4, the medical image reading assistant apparatus 310 may further include a separate artificial neural network configured to generate findings by analyzing medical images in addition to the artificial neural network 430.

Figure 5:
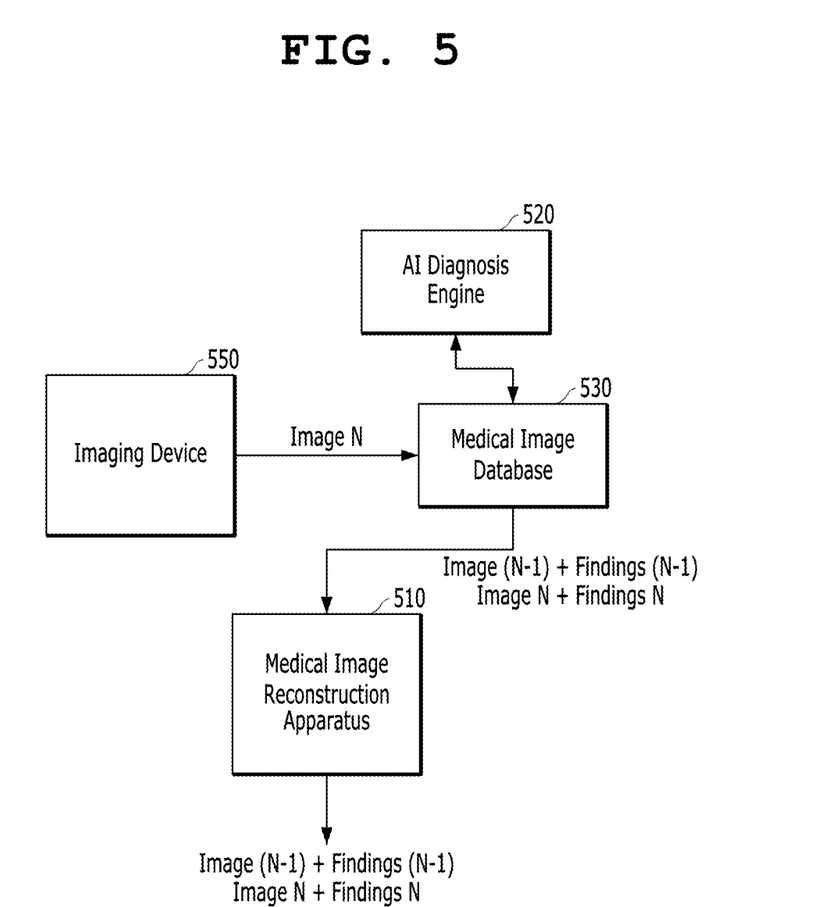
FIG. 5 is a diagram showing an example of a workflow executed in a system including a medical image reading assistant apparatus according to an embodiment of the present invention.

FIG. 5 is a diagram showing an example of a workflow executed in a system including a medical image reading assistant apparatus 510 according to an embodiment of the present invention.

Since the operations of the medical imaging apparatus 550 and medical image database 530 of FIG. 5 are considerably similar to the operations of the medical imaging apparatus 110 and medical image database 130 of FIG. 1, redundant descriptions thereof will be omitted.

In FIG. 5, there is shown an embodiment in which an artificial intelligence (AI) engine having the function of detecting findings is located outside the medical image reading assistant apparatus 510. The at least one processor may receive first findings on a first medical image together with the first medical image via a receiver interface, and may receive second findings on a second medical image together with the second medical image.

In the embodiment of FIG. 5, a training dataset is a dataset in which medical images and findings are stored together, and a training dataset capable of determining the follow-up matching of each finding through medical image-finding pairing may be prepared.

Although the embodiments in which the medical image databases 130, 330, and 530 are located outside are shown in FIGS. 1 to 5, it will be apparent to those skilled in the art that an embodiment in which a database (not shown) is located inside each of the medical image reading assistant apparatuses 110, 310, and 510 may also be implemented according to another embodiment of the present invention.

Figure 6:
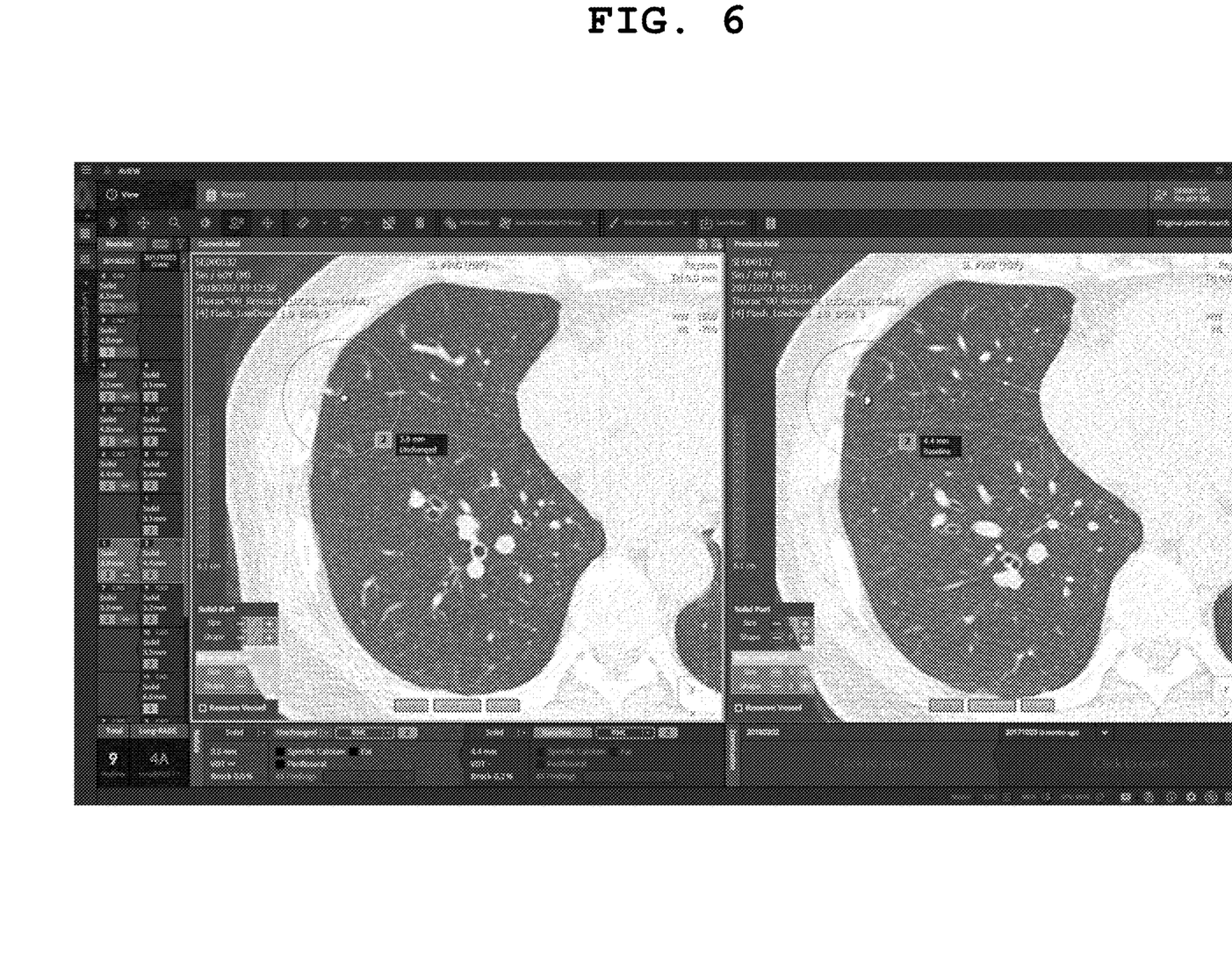
FIG. 6 shows an example of a medical image reading assistant workflow according to an embodiment of the present invention, which illustrates an example of a medical image reading assistant screenshot for lung cancer screening (LCS).

FIG. 6 shows an example of a medical image reading assistant workflow according to an embodiment of the present invention, which illustrates an example of a medical image reading assistant screenshot for lung cancer screening (LCS).

The lung cancer screening shown in FIG. 6 is used to detect lung nodules after reconstruction when executed in a low-dose or ultralow-dose CT. Although various conventional techniques have been proposed for this, it is most important to distinguish between a normal organ and a lesion, and thus an important goal is to obtain an area having a brightness value different from a surrounding brightness value.

Referring to FIG. 6, a recent medical image and a past medical image are visualized together. In this case, findings identified and corresponding to each other in the recent medical image and the past medical image may be visualized together in both of the medical images. On the left side of the screenshot of FIG. 6, findings found in the recent medical image and findings found in a past medical image are arranged alongside each other. As a result of follow-up analysis between the findings found in the two medical images, matched findings are displayed together at the same height on the left side of the screenshot. These mutually matched findings are cross-linked to each other, so that when a finding on either one of the two medical images is selected and activated, the other finding may also be activated.

In the state in which lesion candidates are detected in medical images and findings are generated, the process of analyzing whether each of the findings has a follow-up relationship with a finding on another medical image may be generally performed through non-rigid registration or location-based matching. Alternatively, location-based matching is performed roughly first to narrow the range, and accurate matching between findings may be performed by non-rigid registration. In this case, the location-based analysis technique may be performed based on the result of the segmentation of an organ in the human body. In the case of the lung image shown in FIG. 6, findings on a past medical image and findings on a current medical image may be compared and matched with each other based on landmarks such as the boundary of the lung lobe, the central blood vessel of the lung, and the airway.

A medical image reading assistant method according to an embodiment of the present invention is a method executed in a computing system, and the computing system includes at least one processor.

The medical image reading assistant method according to the present embodiment may be loaded into memory in the form of program instructions, and may be invoked and executed by a processor, a controller, and/or electronic circuit logic designed in a distributed manner.

For example, the process in which the one processor 210 shown in FIG. 2 receives the first medical image included in the time series set of medical images and the second medical image following the first medical image via the receiver interface 250 may be performed as the step of receiving the first medical image and the second medical image.

The process in which the at least one processor 210 generates follow-up information between the first findings on the first medical image and the second findings on the second medical image by comparing the locations of the first findings and the locations of the second findings.

The process in which the at least one processor 210 selects at least some of the first findings as the first valid findings to be provided to the user based on the first threshold of diagnostic assistant information for each of the first findings may be performed as the step of selecting at least some of the first findings as the first valid findings.

The process in which the at least one processor 210 sets the second threshold of diagnostic assistant information for each of the second findings based on the follow-up information and selects at least some of the second findings as the second valid findings to be provided to the user based on the second threshold may be performed as the step of selecting the second valid findings.

The process in which the at least one processor 210 provides the first valid findings and the second valid findings to the user via the user interface 270 may be performed as the step of providing the first valid findings and the second valid findings to the user.

According to the medical image reading assistant technology of the present invention, there may be provided the user interface that analyzes the correlation between finding's information about a past medical image and finding's information about a current medical image based on follow-up information and to applies a different threshold of diagnostic assistant information to a lesion or finding of the current medical image present at the same location as the corresponding lesion or finding of the past medical image, thereby allowing a user to focus more on the clinically significant finding.

According to the present invention, there may be provided the user interface that recognizes contextual information related to follow-up information when the magnitude of finding's information about a current medical image becomes larger than that of corresponding finding's information about a past medical image, the probability of being a lesion increases, or the possibility of malignity increases based on the follow-up information and applies a different threshold of diagnostic assistant information based on the contextual information, thereby allowing a user to focus more on the clinically significant finding.

According to the present invention, there may be provided the user interface that provides a finding having special clinical significance with a visualization element distinct from those of the rest of the findings, thereby allowing a user to focus more on the clinically significant finding.

The method according to an embodiment of the present invention may be implemented in the form of program instructions executable by a variety of computing means and then recorded in a computer-readable storage medium. The computer-readable storage medium may include program instructions, data files, and data structures solely or in combination. Program instructions recorded in the storage medium may have been specially designed and configured for the present invention, or may be known to or available to those who have ordinary knowledge in the field of computer software. Examples of the computer-readable storage medium include all types of hardware devices specially configured to record and execute program instructions, such as magnetic media, such as a hard disk, a floppy disk, and magnetic tape, optical media, such as compact disk (CD)-read only memory (ROM) and a digital versatile disk (DVD), magneto-optical media, such as a floptical disk, ROM, random access memory (RAM), and flash memory. Examples of the program instructions include machine code, such as code created by a compiler, and high-level language code executable by a computer using an interpreter. These hardware devices may be configured to operate as one or more software modules in order to perform the operation of the present invention, and the vice versa.

However, the present invention is not limited to the embodiments. Like reference symbols in the drawings designate like components. The lengths, heights, sizes, widths, etc. introduced in the embodiments and drawings of the present invention may be exaggerated to help to understand the present invention.

Although the present invention has been described with reference to specific details such as the specific components, and the limited embodiments and drawings, these are provided merely to help a general understanding of the present invention, and the present invention is not limited thereto. Furthermore, those having ordinary skill in the art to which the present invention pertains may make various modifications and variations from the above detailed description.

Therefore, the spirit of the present invention should not be defined based only on the described embodiments, and not only the attached claims but also all equivalents to the claims should be construed as falling within the scope of the spirit of the present invention.

What is claimed is:

1. A medical image reading assistant apparatus for assisting reading of a medical image, the medical image reading assistant apparatus comprising a computing system, wherein the computing system comprises:
   a receiver interface configured to receive a first medical image included in a time series set of medical images and a second medical image following the first medical image; and
   at least one processor configured to:
      generate follow-up information between first findings on the first medical image and second findings on the second medical image by comparing locations of the first findings and locations of the second findings, wherein the first findings and the second findings are detected using one or more artificial neural networks;
      select at least some of the first findings as first valid findings to be provided to a user based on a first threshold of diagnostic assistant information for each of the first findings;
      set a second threshold of diagnostic assistant information for each of the second findings based on the follow-up information;
      select second valid findings, among the second findings on the second medical image, to be provided to the user wherein the second valid findings are selected as a first subset of the second findings that correspond to the first findings based on the follow-up information by applying the second threshold; and
      select third valid findings among the second findings on the second medical image, wherein the third valid findings are selected as a second subset of the second findings that do not correspond to the first findings based on the follow-un information by applying the first threshold,
   wherein the at least one processor provides the first valid findings and the second valid findings to the user via a user interface.

2. The medical image reading assistant apparatus of claim 1, wherein the at least one processor is further configured to select a third subset, including second findings within the first subset having diagnostic assistant information greater than diagnostic assistant information of the first findings corresponding to the second findings within the first subset, as fourth valid findings by applying a third threshold smaller than the second threshold to the third subset based on the follow-up information.

3. The medical image reading assistant apparatus wherein the at least one processor is further configured to select a fourth subset of first findings not included in the first valid findings and corresponding to the second valid findings, among the first findings on the first medical image, as fifth valid findings.

4. The medical image reading assistant apparatus of claim 1, wherein the computing system further comprises a first artificial neural network that has learned a function of generating the follow-up information between the first findings and the second findings, and
   wherein the at least one processor is further configured to control the first artificial neural network to identify first subset of second findings corresponding to the first findings, among the second findings on the second medical image.

5. The medical image reading assistant apparatus of claim 1, wherein the computing system further comprises a second artificial neural network that has learned a function of detecting the first findings on the first medical image and the second findings on the second medical image, and
   wherein the at least one processor is further configured to control the second artificial neural network to detect the first findings on the first medical image and the second findings on the second medical image.

6. The medical image reading assistant apparatus of claim 1, wherein the at least one processor is further configured to receive the first findings on the first medical image together with the first medical image and the second findings on the second medical image together with the second medical image via the receiver interface.

7. The medical image reading assistant apparatus of claim 1, wherein the at least one processor is further configured to, in a case where a first valid finding displayed on the first medical image and a second valid finding displayed on the second medical image via the user interface correspond to each other based on the follow-up information, when any one of the first and second valid findings corresponding to each other is selected and visually activated, also visually activate a remaining corresponding valid finding.

8. A medical image reading assistant method for assisting reading of a medical image, the medical image reading assistant method being executed by a computing system, the computing system comprising at least one processor, the medical image reading assistant method comprising:
   receiving, by the at least one processor, a first medical image included in a time series set of medical images and a second medical image following the first medical image via a receiver interface;

generating, by the at least one processor using one or more artificial neural network, follow-up information between first findings on the first medical image and second findings on the second medical image by comparing locations of the first findings and locations of the second findings;

selecting, by the at least one processor, at least some of the first findings as first valid findings to be provided to a user based on a first threshold of diagnostic assistant information for each of the first findings;

setting, by the at least one processor, a second threshold of diagnostic assistant information for each of the second findings based on the follow-up information;

selecting, by the at least one processor, valid findings, among the second findings on the second medical image to be provided to the user, wherein the second valid findings are selected as a first subset of the second findings that correspond to the first findings based on the follow-up information by applying the second threshold;

selecting by the at least one processor, third valid findings among the second findings on the second medical image, wherein the third valid findings are selected as a second subset of the second findings that do not correspond to the first finding a based on the follow-up information by applying the first threshold; and providing, by the at least one processor, the first valid findings and the second valid findings to the user via a user interface.

9. The medical image reading assistant method of claim 8, further comprising:

providing, by the at least one processor, the third valid findings, together with a visualization element distinct from those of the first and second valid findings, to the user via a user interface.

10. The medical image reading assistant method of claim 9, further comprising:

selecting, by the at least one processor, a third subset, including second findings within the first subset having diagnostic assistant information greater than diagnostic assistant information of the first findings corresponding to the second findings within the first subset, as fourth valid findings by applying a third threshold smaller than the second threshold to the third subset based on the follow-up information; and providing, by the at least one processor, the fourth valid findings, together with a visualization element distinct from those of the first to third valid findings, to the user via the user interface.

11. The medical image reading assistant method of claim 9, further comprising:

selecting, by the at least one processor, a fourth subset of first findings not included in the first valid findings and corresponding to the second valid findings, among the first findings on the first medical image, as fifth valid findings; and providing, by the at least one processor, the fifth valid findings, together with a visualization element distinct from those of the first to third valid findings, to the user via the user interface.

12. The medical image reading assistant apparatus of claim 1, wherein the diagnostic assistant information includes at least one of a probability of each finding of the first and second findings, a confidence of each finding of the first and second findings, or a quantitative measurement of size and/or volume of each finding of the first and second findings.

13. The medical image reading assistant method of claim 8, wherein the diagnostic assistant information includes at least one of a probability of each finding of the first and second findings, a confidence of each finding of the first and second findings, or a quantitative measurement of size and/or volume of each finding of the first and second findings.

14. A medical image reading assistant method for assisting reading of a medical image, the medical image reading assistant method being executed by a computing system, the computing system comprising at least one processor, the medical image reading assistant method comprising:

receiving, by the at least one processor, a first medical image included in a time series set of medical images and a second medical image following the first medical image via a receiver interface;

generating, by the at least one processor, follow-up information between first findings on the first medical image and second findings on the second medical image by comparing locations of the first findings and locations of the second findings, wherein the first findings and the second findings are detected using one or more artificial neural networks;

selecting, by the at least one processor, at least some of the first findings as first valid findings to be provided to a user based on a first threshold of diagnostic assistant information for each of the first findings;

setting, by the at least one processor, a second threshold of diagnostic assistant information for each of the second findings based on the follow-up information;

selecting, by the at least one processor, second valid findings, among the second findings on the second medical image, to be provided to the user, wherein the second valid findings are selected as a first subset of the second findings that correspond to the first findings based on the follow-up information by applying the second threshold;

selecting, by the at least one processor, third valid findings among the second findings on the second medical image, wherein the third valid findings are selected as a second subset of the second findings that do not correspond to the first findings based on the follow-up information by applying the first threshold; and providing, by the at least one processor, the first valid findings and the second valid findings to the user via a user interface.

* * * * *